United States Patent
Fukunaga et al.

(10) Patent No.: US 7,054,759 B2
(45) Date of Patent: May 30, 2006

(54) CONCENTRATION MEASURING METHOD

(75) Inventors: Satoshi Fukunaga, Kyoto (JP); Masato Nakayama, Higashikurume (JP)

(73) Assignee: ARKRAY, Inc, Kyoto (JP)

( * ) Notice: Subject to any disclaimer, the term of this patent is extended or adjusted under 35 U.S.C. 154(b) by 28 days.

(21) Appl. No.: 10/500,034

(22) PCT Filed: Dec. 25, 2002

(86) PCT No.: PCT/JP02/13562

§ 371 (c)(1),
(2), (4) Date: Jun. 24, 2004

(87) PCT Pub. No.: WO03/056312

PCT Pub. Date: Jul. 10, 2003

(65) Prior Publication Data

US 2005/0107956 A1    May 19, 2005

(30) Foreign Application Priority Data

Dec. 27, 2001    (JP) .............................. 2001-395981

(51) Int. Cl.
   *G06N 31/00*    (2006.01)
(52) U.S. Cl. .......................... 702/23; 702/19; 702/22; 435/7.1; 435/287.2; 73/861.07; 250/253
(58) Field of Classification Search .................. 702/19, 702/22; 435/7.1, 287.2; 73/861.07; 250/253
See application file for complete search history.

(56) References Cited

U.S. PATENT DOCUMENTS 4,558,012 A * 12/1985 Nygren et al. .............. 436/501

5,420,042 A    5/1995 Schafer et al.
2003/0113713 A1 *  6/2003 Glezer et al. ................... 435/5
2004/0053322 A1 *  3/2004 McDevitt et al. ............ 435/7.1

FOREIGN PATENT DOCUMENTS

JP    4-249744    9/1992

(Continued)

OTHER PUBLICATIONS

EPA-Method 9014, 'Hazard Waste Test: Titrimeteric and Manual Spectrophotometeric Determinative Methods for Cyanide', Dec. 1996, EPA Publication, pp. 9014-1 to 9014-7.*

(Continued)

*Primary Examiner*—Patrick Assouar
*Assistant Examiner*—Elias Desta
(74) *Attorney, Agent, or Firm*—Hamre, Schumann, Mueller & Larson, P.C.

(57) ABSTRACT

A concentration measuring method includes selecting a calibration curve optimum for computing the concentration of a measurement target substance from a plurality of calibration curves based on an output from a reaction system containing the target substance and a reactant capable of reacting with the target substance, and computing the concentration of the target substance based on the optimum calibration curve and the output. Each of the calibration curves is prepared based on a plurality of outputs generated upon lapse of a same reaction time from a plurality of standard reaction systems each containing a standard reagent of a known different concentration and the reactant. The plurality of calibration curves differ from each other in reaction time based on which the calibration curves are prepared.

11 Claims, 8 Drawing Sheets

FOREIGN PATENT DOCUMENTS

| | | |
|---|---|---|
| JP | 5-99930 | 4/1993 |
| JP | 6-167501 | 6/1994 |
| JP | 6-249856 | 9/1994 |
| JP | 7-12733 | 1/1995 |
| WO | WO 02/29015 | 4/2002 |

OTHER PUBLICATIONS

Khan et al. 'Determination of Trace Amounts of Copper (II) by Using Catalytic Redox Reaction between Methylene Blue and Ascorbic Acid', Oct. 2001, Japan Society for Analytical Chemistry Publication, vol. 17, pp. 1195-1197.*

* cited by examiner

CONCENTRATION MEASURING METHOD

TECHNICAL FIELD

The present invention relates to a concentration measuring method for computing the concentration of a target substance to be measured based on an output value from a reaction system containing the target substance, and a calibration curve (which shows the relationship between the concentration of the target substance and the output value).

BACKGROUND ART

A conventional method for measuring the concentration of an antigen in an analyte such as urine may utilize the combination of an antigen-antibody reaction and an optical technique. In this method, for instance, an analyte is mixed with an antibody for causing an antigen-antibody reaction, and the concentration is computed based on the absorbance outputted when the reaction system is irradiated with light. In this method, as long as the antigen concentration in the reaction system does not exceed a specific range, the measured absorbance with an increasing concentration of the antigen. However, when the antigen concentration in the reaction system exceeds the specific range, a phenomenon (prozone phenomenon) is observed wherein the measured absorbance decreases with an increasing concentration of the antigen. Such a phenomenon occurs not only in a antigen-antibody reaction but also in biochemistry in general. (Hereinafter, this phenomenon is referred to as "prozone-like phenomenon" inclusively of those in biochemistry.)

In a system in which the prozone-like phenomenon occurs, the computed concentration of the target substance may be lower than the actual concentration due to lowered absorbance. To eliminate such a disadvantage, the absorbance need be measured again after the analyte is diluted, for example.

However, to perform the measurement of the same analyte a plurality of times is not desirable in view of the high cost of the antigen. Further, a smaller number of times of measurement is preferable for facilitation of the measuring process. Although the prozone-like phenomenon does not occur in the measurement of e.g. the glucose level in urine, such measurement suffers from another problem that measurement resolution is poor in a high concentration range. Therefore, a system in which the prozone-like phenomenon does not occur also suffers from low measurement accuracy in a high concentration range.

DISCLOSURE OF THE INVENTION

An object of the present invention is to easily and inexpensively prevent the deterioration of the measurement accuracy in the measurement of a sample solution of a high concentration due to the influence of the prozone-like phenomenon or the reduction of the resolution in a high concentration range.

According to a first aspect of the present invention, there is provided a concentration measuring method comprising: selecting a calibration curve optimum for computing concentration of a measurement target substance from a plurality of calibration curves based on an output from a reaction system containing the target substance and a reactant capable of reacting with the target substance; and computing the concentration of the target substance based on the optimum calibration curve and the output. Each of the calibration curves is prepared based on a plurality of outputs generated upon lapse of a same reaction time from a plurality of standard reaction systems each containing a standard reagent of a known different concentration and the reactant. The plurality of calibration curves differ from each other in reaction time based on which the calibration curves are prepared.

In a preferred embodiment, the plurality of calibration curves include a first calibration curve to be selected when the concentration of the target substance is predicted to be higher than a predetermined concentration threshold, and a second calibration curve to be selected when the concentration of the target substance is predicted to be lower than the concentration threshold. The first calibration curve is prepared based on an output measured in an initial stage of the reaction between a standard substance of a known concentration and the reactant, and the second calibration curve is prepared based on an output measured after the output as the base for the preparation of the first calibration curve is measured.

Preferably, in this case, when a second concentration computed by using the second calibration curve is predicted to be larger than the concentration threshold, a first concentration computed by using the first calibration curve is compared with the second concentration, and a larger one of the first and second concentrations is adopted as a conclusive computation result. On the other hand, when the second concentration value is predicted to be lower than the concentration threshold, it is preferable to determine whether or not the second concentration value reflects the concentration of the target substance. When the second concentration value reflects the concentration of the target substance, the second concentration value is adopted as a conclusive computation result. When the second concentration value does not reflect the concentration of the target substance, the first concentration value computed by using the first calibration curve is adopted as a conclusive computation result.

The selection between the first calibration curve and the second calibration curve may be performed based on the first concentration value computed by using the first calibration curve. For instance, when the first concentration is predicted to be higher than the concentration threshold, the first concentration is adopted as the conclusive computation result. On the other hand, when the first concentration is predicted to be lower than the concentration threshold, the second concentration computed by using the second calibration curve is adopted as a conclusive computation result.

For instance, whether the concentration of the target substance is higher or lower than the concentration threshold may be predicted based on whether or not the output is higher than a predetermined output threshold.

The concentration threshold may be set to lie in a concentration range in which the second calibration curve has high linearity or to the concentration corresponding to an intersection of the first calibration curve and the second calibration curve.

In the present invention, no less than three calibration curves may be prepared for the selection of the optimum calibration curves. Specifically, a plurality of calibration curves may be prepared by measuring, at a plurality of (no less than three) measurement time points, outputs from the plurality of standard reaction systems each containing a standard reagent of a known different concentration and the reactant, each of the calibration curves corresponding to a respective one of the measurement points. Preferably, in this case, the selection of the optimum calibration curve is performed based on an output measured in a time period in which the reaction between the target substance and the reactant is in an initial stage.

According to a second aspect of the present invention, there is provided a concentration measuring method for computing concentration of a measurement target substance based on an output from a reaction system containing the target substance and a reactant capable of reacting with the target substance, and a calibration curve showing a relationship between the concentration of the target substance and the output. The calibration curve is prepared by performing time-wise measurement, in a predetermined time period, of outputs from a plurality of standard reaction systems each containing a standard reagent of a known different concentration and the reactant, and collecting a set of maximum outputs for the respective reaction systems.

According to a third aspect of the present invention, there is provided a concentration measuring method for computing concentration of a measurement target substance based on an output from a reaction system containing the target substance and a reactant capable of reacting with the target substance, and a specific calibration curve showing a relationship between the concentration of the target substance and the output. The specific calibration curve is prepared as a composite of a first calibration curve and a second calibration curve. The first calibration curve is prepared based on an output measured in an initial stage of the reaction between a standard substance of a known concentration and the reactant. The second calibration curve is prepared based on an output measured after the output as the base for the preparation of the first calibration curve is measured. The specific calibration curve comprises a higher concentration portion for a concentration range higher than an intersection concentration which corresponds to an intersection of the first calibration curve and the second calibration curve, and a lower concentration portion for a concentration range lower than the intersection concentration. The higher concentration portion comprises a portion of the second calibration curve for a concentration range higher than the intersection concentration. The lower concentration portion comprises a portion of the first calibration curve for a concentration range lower than the intersection concentration.

For instance, the output value in the present invention may be a response value (optical response value) obtained when the reaction system is irradiated with light. Alternatively, the output value may be an electrical response value obtained when a voltage is applied to the reaction system or a current is caused to flow through the reaction system. Herein, the "optical response value" includes absorbance, turbidity and transmittance, for example. The "absorbance" includes that determined based on the amount of light passed through a liquid phase reaction system provided in a reaction vessel or that determined based on the amount of light reflected by a reaction system retained by a solid phase such as a porous member.

BEST MODE FOR CARRYING OUT THE INVENTION

The best mode for carrying out the present invention will be described below with reference to the accompanying drawings.

The present invention relates to a method for computing the concentration of a measurement target substance based on an optical response value obtained upon irradiation of a reaction system with light, and a calibration curve. Herein, the "calibration curve" means one that shows the relationship between the concentration of the target substance and the optical response value, and at least includes those expressed as a function and as a table.

Figure 1A:
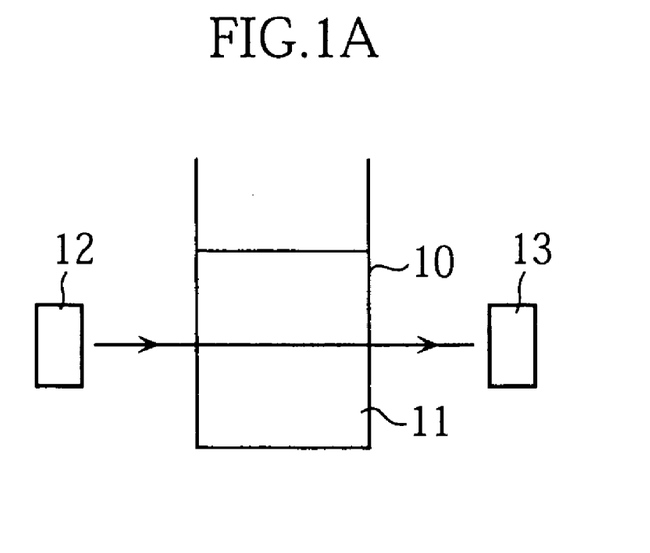
FIGS. 1A and 1B are schematic views illustrating a method for measuring an optical response value.
Figure 1B:
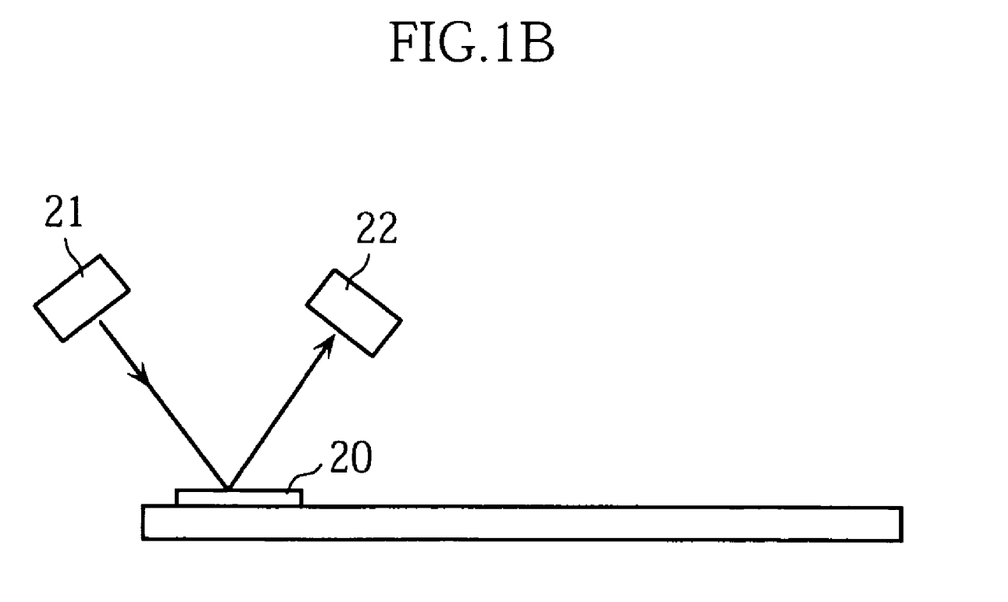

The reaction system includes a measurement target substance, and a reactant for reacting with the target substance. The reaction system changes its color or turbidity, for example, in accordance with the amount of the reaction product generated by the reaction between the target substance and the reactant. Accordingly, the optical response in the reaction system changes depending on the progress of the reaction or the amount of the target substance. The reaction system may comprise a reaction solution 11 retained in a vessel 10 as shown in FIG. 1A or a solid phase 20 retaining a reaction solution as shown in FIG. 1B. The solid phase 20 may be made of a material having a high water absorption, such as paper or a felt-like material.

Examples of target substance include albumin, glucose, amylase and creatinine. In addition to the concentration measurement of a particular substance, the present invention is also applicable to the measurement of the total amount of a plurality of similar substances such as the total amount of protein or cholesterol. The reactant may comprise a color indicator selected depending on the target substance.

The optical response may be obtained as absorbance, turbidity or transmittance. In the reaction system shown in FIG. 1A, a light emitting element 12 irradiates the reaction system with light, and the light transmitted through the reaction system is received by a light receiving element 13. In this reaction system, the optical response is computed based on the amount of light received by the light receiving element 13 and the amount of light incident on the reaction system (e.g. the amount of light emitted from the light emitting element 12). In the reaction system shown in FIG. 1B, a light emitting element 21 irradiates the reaction system with light, and a light receiving element 22 receives the reflected light. In this reaction system, the optical response is computed based on the amount of light received by the light receiving element 22 and the amount of light incident on the reaction system (e.g. the amount of light emitted from the light emitting element 21). In the reaction system shown in FIG. 1B, the transmittance or turbidity cannot be measured, and the optical response is measured as the absorbance.

In the concentration measuring method according to a first embodiment of the present invention, the concentration computation is performed by selectively using one calibration curve for a sample of a relatively high concentration and another calibration curve for a sample of a relatively low concentration. The specific manner for selectively using the two calibration curves (1), (2) will be described later, and the reasons for using the two calibration curves (1), (2) will be described first.

Figure 2:
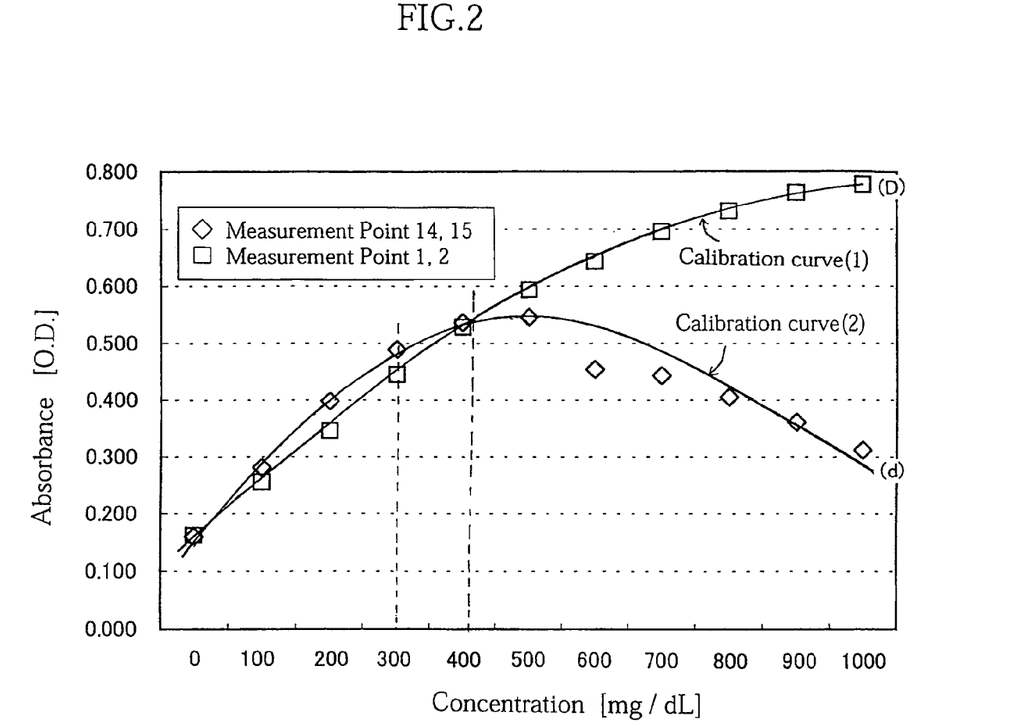
FIG. 2 is a graph showing a first and a second calibration curves (1), (2) used for the concentration computation according to a first embodiment of the present invention.

FIG. 2 shows two calibration curves (1), (2) to be utilized when the target substance is protein (human serum albumin). Specifically, these calibration curves (1), (2) may be used in measuring the protein concentration in human urine, for example.

The calibration curve (1) is prepared by using a reaction solution of a high protein concentration (1000 mg/dL) and based on the absorbance measured in the initial stage of the reaction. Herein, the "initial stage of the reaction" means a stage of reaction in the high concentration reaction solution in which the absorbance varying with time becomes maximum or nearly maximum.

The calibration curve (2) is prepared by using a reaction solution of a low protein concentration (100 mg/dL) and based on the absorbance measured in the reaction equilibrium stage in which the reaction solution reaches an equilibrium or nearly equilibrium state. Herein, the "reaction equilibrium stage" means a stage of reaction in the low concentration reaction solution in which the absorbance varying with time asymptotically approaches a constant value or exhibits a similar behavior.

Figure 3:
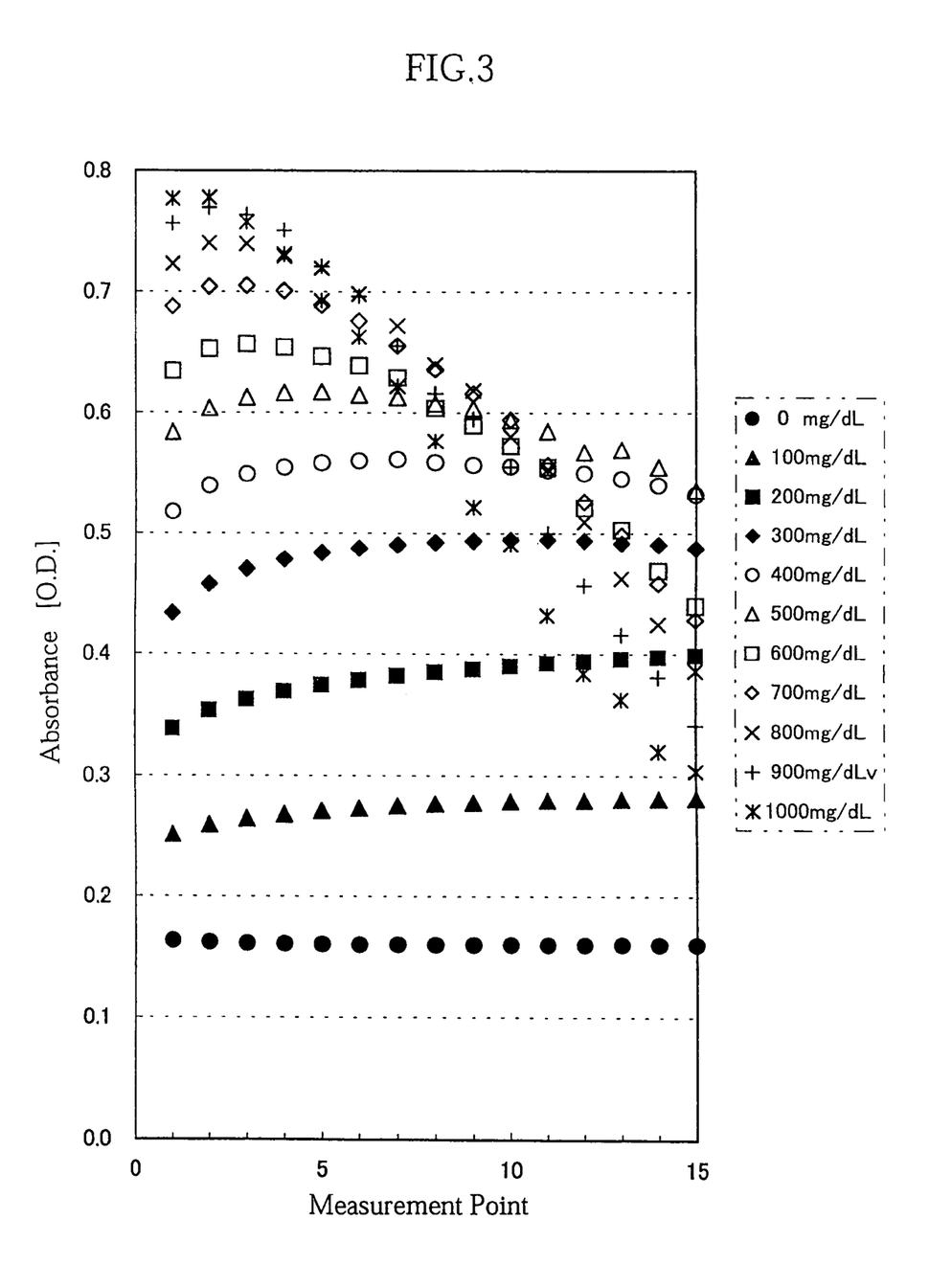
FIG. 3 is a graph showing the change of absorbance with time of a plurality of standard reaction solutions of different concentrations.

FIG. 3 shows the absorbance, varying with time, of eleven protein standard solutions when caused to react with a reactant, the standard solutions having different protein concentrations ranging from 0 to 1000 mg/dL. Specifically, the absorbance was measured a plurality of times at intervals of 21.5 seconds after the start of the reaction, and respective measurement time points are represented as measurement point 1, measurement point 2 and so on in FIG. 3. For example, the measurement point 10 corresponds to a reaction time of 215 seconds (21.5 seconds×10). In the following description and other figures, the term "measurement point" is used in the same sense as described above.

In determining the change of absorbance with time, pigment-metal bond was used for reaction between the target substance and the reactant. Specifically, the reactant was a complex compound of bromopyrogallol red (pigment) and indium (metal). Each of the protein standard solutions was prepared by adding human serum albumin (HAS) to healthy pooled urine to adjust the protein concentration. The absorbance was measured using an automatic urine quantitative analyzer (Aution Master UM3410: available from ARKRAY, INC.) at a measurement wavelength of 600 nm.

As shown in FIG. 3, for a protein standard solution of a low concentration (100 mg/dL), the absorbance asymptotically approaches a constant value at the measurement points 14, 15 to become constant. Thus, when the protein standard solution of a low concentration (100 mg/dL) is used, the reaction equilibrium is almost reached at the measurement points 14, 15. On the other hand, for a protein standard solution of a high concentration, the absorbance tends to decrease as the reaction time increases. This means that the prozone-like phenomenon occurs in a protein standard solution having a concentration of no lower than 400 mg/dL. The higher the protein concentration in the protein standard solution is, the smaller the measurement point at which the prozone phenomenon occurs is. For example, the absorbance of a protein standard solution having a medium concentration (400 mg/dL) reaches a peak value at the measurement point 7, whereas the absorbance of a protein standard solution having a high concentration (1000 mg/dL) reaches a peak value at the measurement points 1, 2.

As can be understood from the results shown in FIG. 3, in the case where the concentration of the target substance (e.g. protein) in the reaction solution is high, it is preferable to use the calibration curve (1) (See FIG. 2) prepared based on the absorbance measured around the time when the absorbance reaches a peak. On the other hand, in the case where the concentration of the target substance (e.g. protein) in the reaction solution is low, it is preferable to use the calibration curve (2) (See FIG. 2) prepared based on the absorbance measured when or immediately before the reaction equilibrium is reached.

The reason for selectively using the two calibration curves (1), (2) shown in FIG. 2 can be well understood from the above description given with reference to FIG. 3. However, a question may still arise as to why it is insufficient to solely use the calibration curve (1) with respect to all the concentration range for avoiding the trouble of selectively using two calibration curves (1), (2). In other words, the meaning of using the calibration curve (2) with respect to a sample of a relatively low concentration may be questioned. Such a question will be answered by the analysis of the dynamic range and repeatability given below.

Figure 4:
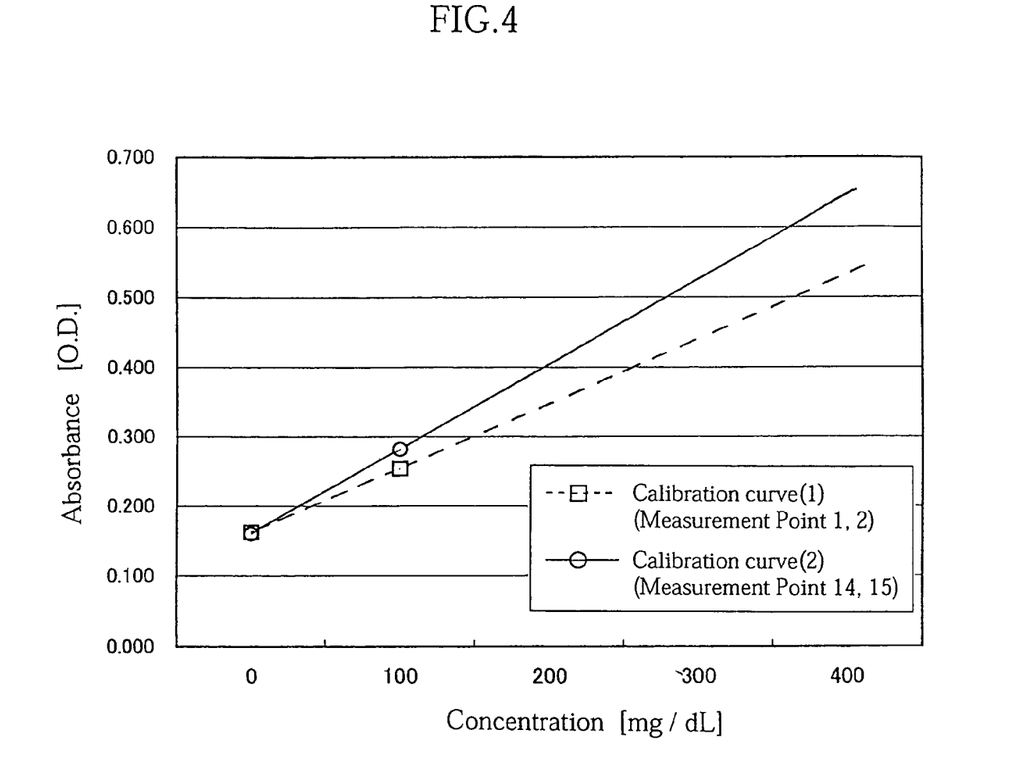
FIG. 4 is a graph showing the dynamic range of a standard reaction solution.

The dynamic range was examined by using two protein standard solutions having HSA concentrations of 0 mg/dL and 100 mg/dL, respectively. Specifically, the absorbance at the measurement points 1, 2 and the measurement points 14, 15 was measured in the same manner as described above, and the dynamic range was examined based on the average for the measurement points 1, 2 and the average for the measurement points 14, 15 computed with respect each of the solutions. The results are given in Table 1 below and in FIG. 4. The dynamic range is larger when the calibration curve (2) is used than when the calibration curve (1) is used.

TABLE 1

|  | Standard Solution Concentration | | Dynamic |
| --- | --- | --- | --- |
|  | 0 (mg/dL) | 100 (mg/dL) | Range |
| Absorbance at Measurement Points 1, 2 (O.D.) | 0.162 | 0.254 | 0.0916 |
| Absorbance at Measurement Points 14, 15 (O.D.) | 0.160 | 0.282 | 0.122 |

To examine the repeatability, the absorbance of three patients' urine A, B, C of different concentrations was measured for computation of the concentrations. Repeatability was examined with respect to the concentrations computed by using the calibration curve (1) and those computed by using the calibration curve (2). Specifically, the repeatability was examined based on three items, i.e., the average concentration, the standard deviation of concentration (S.D.) and the coefficient of variation of concentration (C.V.). For the examination of the repeatability, ten samples were used with respect to each of the patients' urine A, B, C, and the absorbance as the base of the concentration computation was measured in the same manner as described before.

FIG. 2 shows the computation results of the three items.

TABLE 2

| | Calibration Curve (1) Measurement Points 1, 2 | | | Calibration Curve (2) Measurement Points 14, 15 | | |
|---|---|---|---|---|---|---|
| | Patient Urine A | Patient Urine B | Patient Urine C | Patient Urine A | Patient Urine B | Patient Urine C |
| Average Value (mg/dL) | 11.5 | 24.6 | 107.8 | 12.6 | 29.9 | 111.6 |
| S.D. | 2.6 | 2.7 | 3.8 | 1.8 | 1.8 | 3.4 |
| C.V. (%) | 22.7 | 11.0 | 3.5 | 14.6 | 6.1 | 3.0 |

The patients' urine A, B, C has considerably low concentrations. The standard deviation (S.D.) and the coefficient of variation of deviation (C.V.) in these samples having such low concentrations are lower when the calibration curve (2) is used than when the calibration curve (1) is used. This result indicates that the use of the calibration curve (2) for a low concentration range provides better repeatability (less measurement error).

Thus, the examination of the dynamic range and the repeatability indicates that the use of the calibration curve (2) is more preferable than the use of the calibration curve (1) with respect to a low concentration range.

In view of the above facts, in this embodiment, the calibration curve (1) prepared based on the average absorbance for the measurement points 1, 2 is used for a reaction solution having a relatively high concentration, whereas the calibration curve (2) prepared based on the average absorbance for the measurement points 14, 15 is used for a reaction solution having a relatively low concentration. It is to be noted that each calibration curve is prepared based on the average for two measurement points for lessening the influences by measurement errors.

Figure 5:
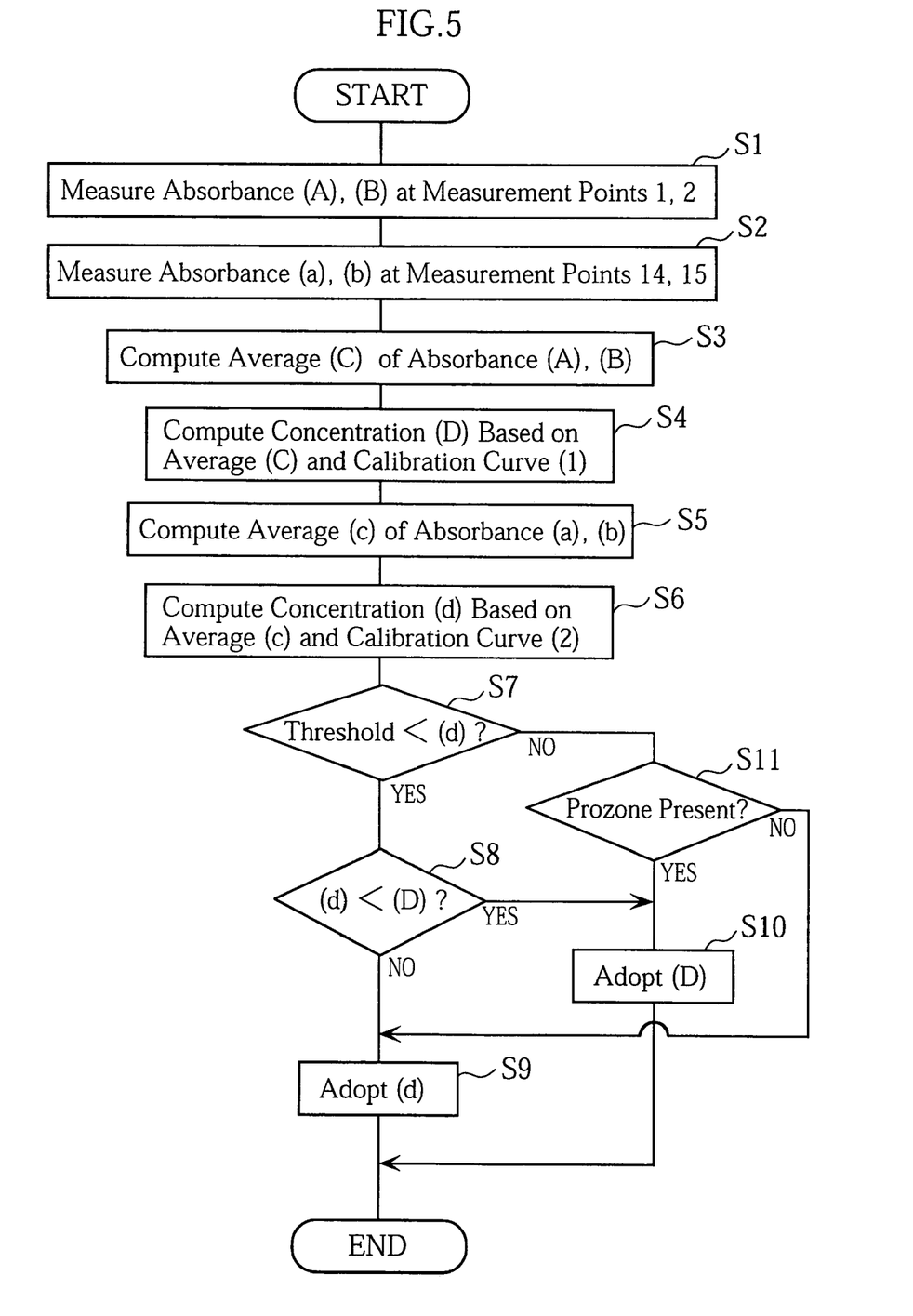
FIG. 5 is a flow diagram showing an example of concentration computation process.

Next, the concentration computation process will be described with reference to FIG. 2 and in accordance with the flowchart shown in FIG. 5. First, the absorbance (A), (B) at the measurement points 1, 2 is measured (S1), and the absorbance (a), (b) at the measurement points 14, 15 is measured (S2). Of course, the absorbance may be measured at constant intervals (e.g. every 21.5 seconds), and the measurements (absorbance) corresponding to the measurement points 1, 2 and the measurement points 14, 15 may be picked up from the group of the measurements.

Subsequently, the average (C) of the absorbance (A), (B) at the measurement points 1, 2 is computed (S3), and a first concentration (D) is computed based on the average (C) and the calibration curve (1) (S4). Further, the average (c) of the absorbance (a), (b) at the measurement points 14, 15 is computed (S5), and a second concentration (d) is computed based on the average (c) and the calibration curve (2) (S6).

Subsequently, a determination is made as to whether or not the second concentration (d) is higher than a predetermined concentration computation threshold (S7). By this, whether the concentration of the target substance is relatively high or relatively low is predicted. Herein, the concentration computation threshold is set to lie in the concentration range (from 200 to 300 mg/dL) in which both of the two calibration curves (1), (2) have high linearity or to the concentration (about 400 mg/dL) corresponding to the intersection of the calibration curves (1) and (2). The determination as to whether or not the concentration of the target substance is higher than the concentration computation threshold may be performed based on whether or not the optical response (e.g. absorbance) is higher than a predetermined optical response threshold and without computing the second concentration (d).

When the second concentration (d) is determined to be higher than the concentration computation threshold (S7: YES), the first concentration (D) and the second concentration (d) are compared (S8), and the higher of these two is adopted (S9, S10). Specifically, when the first concentration (D) is higher than the second concentration (d) (S8: YES), the first concentration (D) is adopted as the conclusive computation result. When the second concentration (d) is higher than the first concentration (D) (S8: NO), the second concentration (d) is adopted as the conclusive computation result (S9).

As can be understood from FIG. 2, the calibration curve (2) is prepared based on the absorbance in the case where the prozone-like phenomenon is observed, whereas the calibration curve (1) is prepared based on the absorbance in the case where the prozone phenomenon is absent. Therefore, when the computation result obtained based on the calibration curve (1) is compared with that obtained based on the calibration curve (2) for adoption of a higher value, the value obtained based on the calibration curve (1) is adopted in a concentration range in which the computation result obtained based on the calibration curve (2) is lower than the actual concentration due to the prozone-like phenomenon. Therefore, it is possible to realize computation which is free from the influences of the prozone-like phenomenon.

On the other hand, when the second concentration (d) is determined to be lower than the concentration computation threshold (S7: NO), a determination is made as to whether the low value of the second concentration (d) is attributable to the prozone-like phenomenon or whether the concentration is actually low (S11). If the low value of the second concentration (2) is due to the prozone-like phenomenon (S11: YES), the first concentration (D), which is the value computed based on the calibration curve (1), is adopted as a conclusive computation result (S10). If the prozone-like phenomenon is determined to be absent and the second concentration (d) is simply low (S11: NO), the second concentration (d) is adopted, as is, as a conclusive computation result (S9).

In the above process, the computation result based on the calibration curve (1) is adopted with respect to a relatively high concentration range in which the computation based on the calibration curve (2) is influenced by the prozone-like phenomenon. Thus, the simple technique of selectively using the calibration curves (1), (2) makes it possible to obtain a proper computation result with respect to a high concentration range while eliminating the need for repeating the measurement and minimizing the influences of the prozone-like phenomenon. With respect to a low concentration range, on the other hand, the second concentration (d) computed by using the calibration curve (2) is adopted. Therefore, as can be understood from the above results of the examination for repeatability, the repeatability in the low concentration range is improved.

Figure 6:
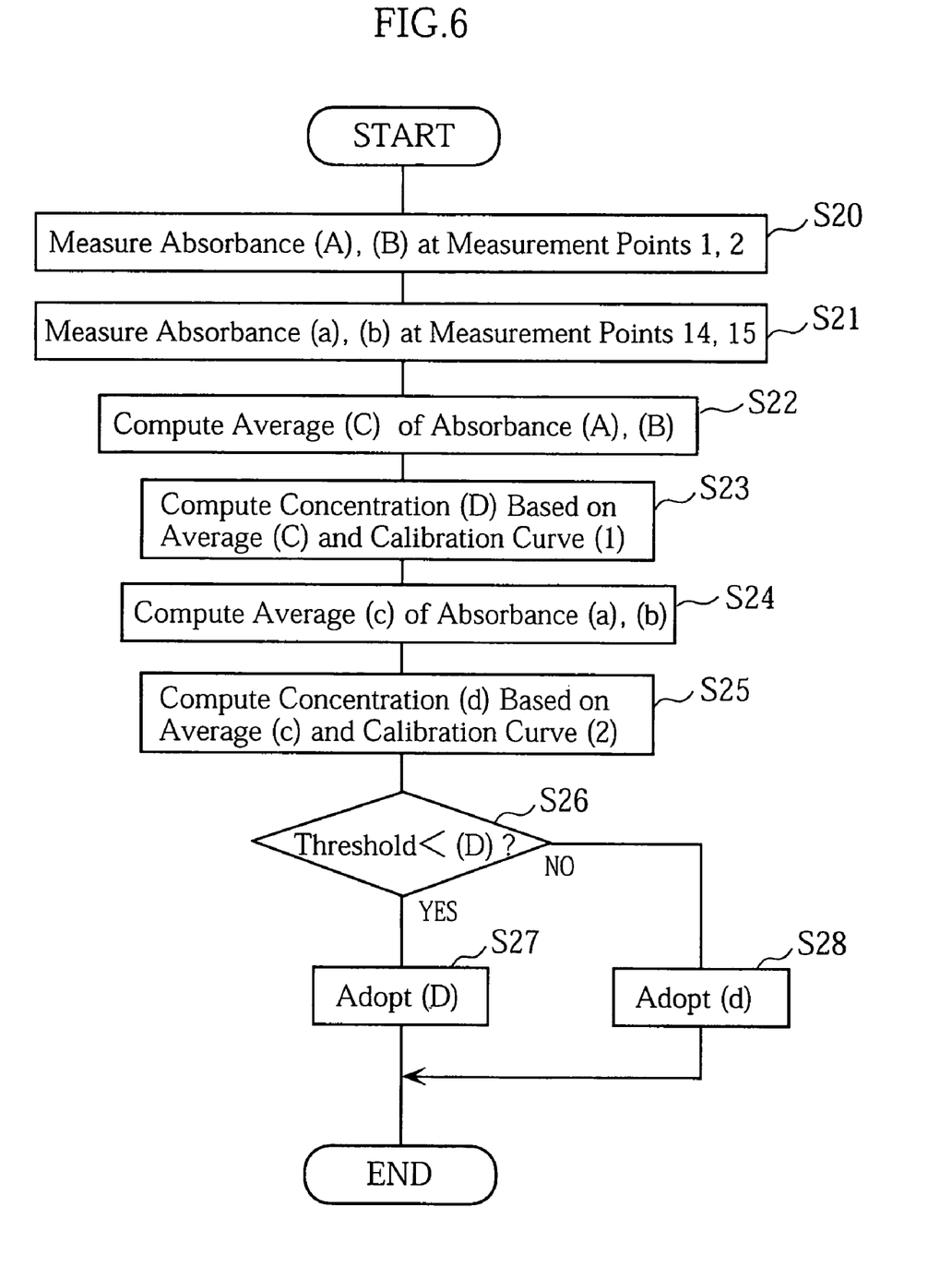
FIG. 6 is a flow diagram showing another example of concentration computation process.

The above-described advantages can be obtained also when the concentration computation is performed following the process steps shown in FIG. 6. First, in this concentration computation process, a first concentration (D) and a second concentration (d) are computed in the same manner as in S1–S6 of the flow shown in FIG. 5 (S20–S25). Subsequently, a determination is made as to whether or not the first concentration (D) is higher than a concentration computation threshold (S26). Specifically, by comparing the first concentration (D), as the reference, with the concentration computation threshold, a determination is made as to whether the concentration of the target substance is relatively high or relatively low. This process step differs from that of the concentration computation shown in FIG. 5 in which a determination is made as to whether or not the second concentration (d) computed by using the calibration curve (2) is larger than a concentration computation threshold.

When the first concentration (D) is larger than the concentration computation threshold in the determination of S26 (S26: YES), i.e., when the concentration is determined to be relatively high, the first concentration (D) obtained by the computation based on the calibration curve (1) is adopted as a conclusive computation result (S27). When the first concentration (D) is lower than the concentration computation threshold (S26: NO), i.e., when the concentration is determined to be relatively low, the second concentration (d) obtained by the computation based on the calibration curve (2) which provides enhanced repeatability is adopted as a conclusive computation result (S28). The above concentration computation process is advantageous in that detection of the prozone-like phenomenon is unnecessary.

Also in the concentration computation process shown in FIG. 6, the concentration computation threshold is set to lie in the concentration range (from 200 to 300 mg/dL) in which both of the two calibration curves (1), (2) have high linearity or to the concentration (about 400 mg/dL) corresponding to the intersection of the calibration curves (1) and (2). When the concentration computation threshold is set in the latter manner, the larger one of the two values, i.e., of the computation result obtained based on the calibration curve (1) and that obtained based on the calibration curve (2) is adopted as a conclusive computation result in S27 and S28. In other words, the result will be the same as that in the case where the first concentration (D) is compared with the second concentration (d) and the larger one is adopted as a conclusive computation result. In a computation process similar to the above, the following calibration curve may be utilized. In this calibration curve, the intersection of the calibration curves (1) and (2) is set as a boundary, and the calibration curve (1) is utilized for a concentration range higher than the boundary, whereas the calibration curve (2) is utilized for a concentration range lower than the boundary. In this case, advantageously, there is no need for comparing the first concentration (D) or the second concentration (d) with a concentration computation threshold or comparing the first concentration (D) with the second concentration (d).

Figure 7:
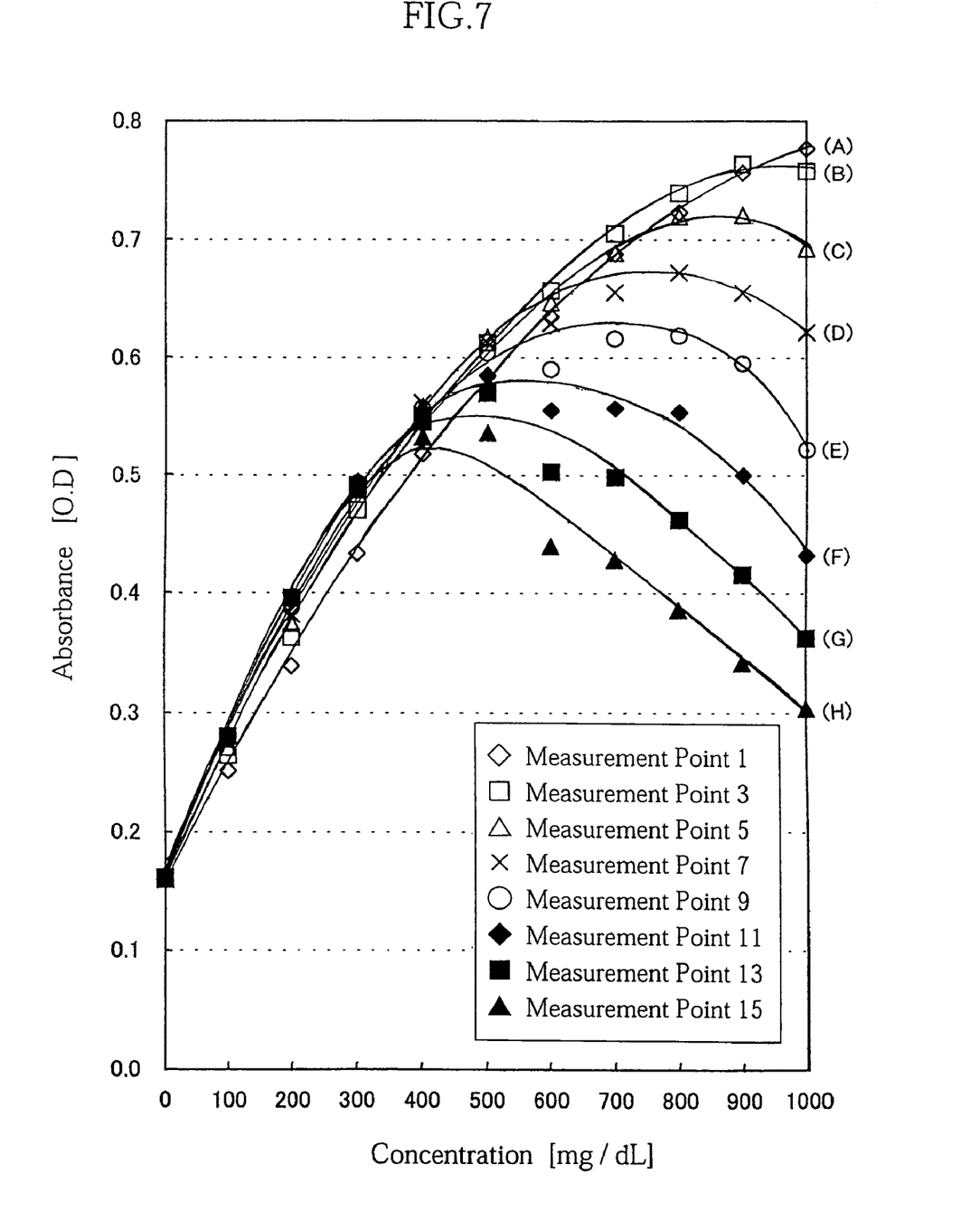
FIG. 7 is a graph showing a plurality of calibration curves (A)–(H) used for the concentration computation according to a second embodiment of the present invention.

Next, a concentration measuring method according to a second embodiment of the present invention will be described. In this concentration measuring method, a plurality of calibration curves (A)–(H) shown in FIG. 7 are selectively used for the concentration computation. The calibration curves (A)–(H) are prepared based on the plurality of absorbance measurements used in preparing the graph of FIG. 3. Specifically, the absorbance measurements are grouped for each of the measurement points, and each of the calibration curves (A)–(H) is formed to correspond to a respective group (respective measurement point). In other words, the calibration curves (A)–(H) are prepared with respect to different reaction times (a plurality of measurement points).

Figure 8:
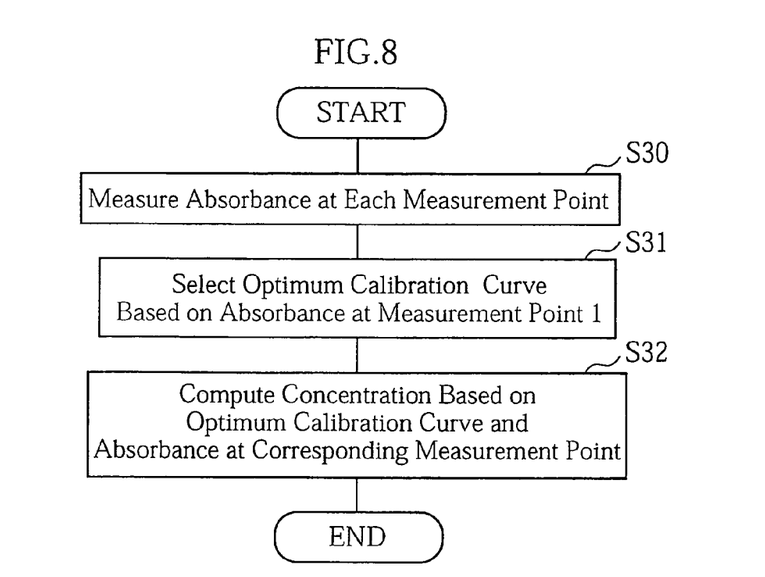
FIG. 8 is a graph showing an example of concentration computation process.

As shown in FIG. 8, in performing the concentration computation using the calibration curves (A)–(H), the absorbance is measured at each of the measurement points (S30). Subsequently, the one which is optimum for the concentration computation is selected from the calibration curves (A)–(H) based on the absorbance at the measurement point 1 (S31). As is clear from FIG. 3, a higher concentration of the target substance provides a higher initial absorbance (the absorbance at the measurement point 1). Therefore, the concentration of the target substance can be predicted properly based on the initial measurement value. Therefore, in S31, the optimum calibration curve can be selected based on the predicted value. Specifically, for a higher value of the predicted absorbance, a calibration curve based on the absorbance at a smaller measurement point (shorter reaction time) is selected. For instance, when the absorbance at the measurement point 1 is relatively high and the concentration is predicted to be no lower than 900 mg/dL, the calibration curve (A) is selected. When the absorbance at the measurement point 1 is relatively low and the concentration is predicted to be no higher than 150 mg/dL, the calibration (H) is selected.

Finally, the concentration computation is performed based on the optimum calibration curve and the measured absorbance at the measurement point corresponding to the calibration curve (S32).

As can be predicted from FIG. 3, when the optimum calibration curve is selected in such a manner as in S31, the absorbance at the measurement point corresponding to the selected optimum calibration curve is the maximum or nearly maximum value of the time-wise varying absorbance. Therefore, the computation method of this embodiment makes it possible to obtain a proper concentration computation result while suppressing the influences of the prozone-like phenomenon.

In this embodiment, though the preparation of a plurality of calibration curves is necessary, it is unnecessary to detect the prozone-like phenomenon or to determine a concentration computation threshold to select the calibration curve based on comparison with the threshold. Therefore, the concentration measurement can be performed by a simple process. Moreover, since a calibration curve prepared based on the absorbance at a relatively large measurement point (long reaction time) is selected in measuring a relatively low concentration, the repeatability in measuring the low concentration substance can be improved.

Although the concentration computation by using calibration curves (A)–(H) prepared based on eight measurement points is described in this embodiment, more than or less than eight calibration curves may be utilized. Further, as is in the concentration measurement method of the first embodiment, a plurality of calibration curves may be prepared as the average for two measurement points, and the concentration computation may be performed by the same process steps using the calibration curves.

Figure 9:
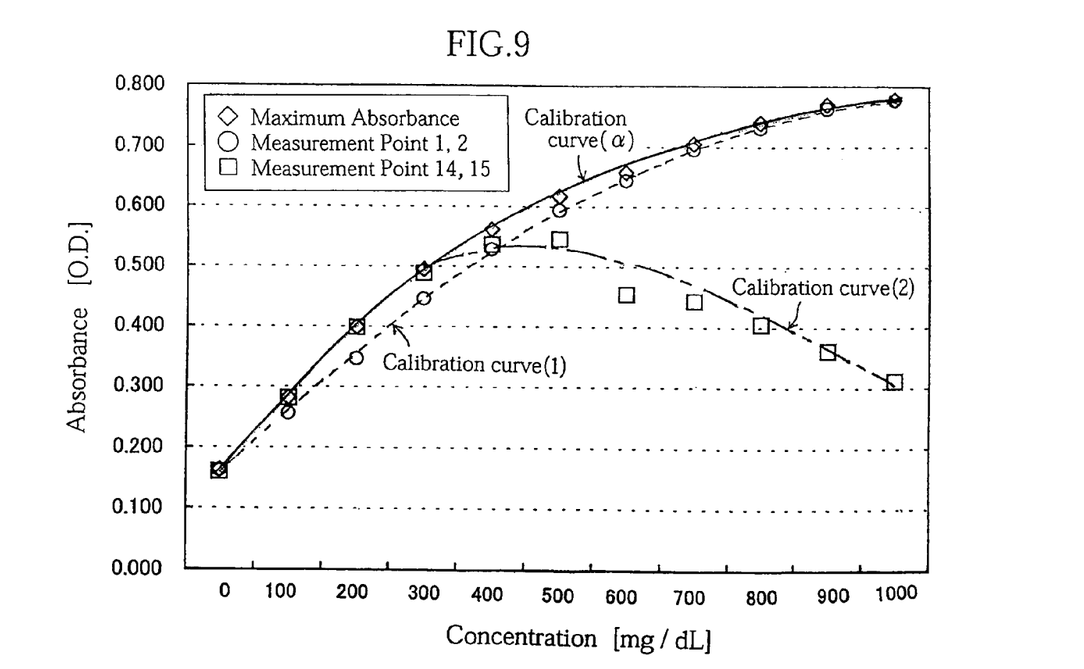
FIG. 9 is a graph for describing the calibration curve ($\alpha$).

In this embodiment, a plurality of calibration curves for respective measurement points are prepared, and the concentration is computed based on the maximum or nearly maximum value of the time-wise varying absorbance. In a computation process similar to the above, use may be made of the calibration curve (α) indicated by a solid line curve in FIG. 9. The calibration curve (α) is prepared by collecting the maximum value of the absorbance from a plurality of plot points for a same given concentration in FIG. 3. In FIG. 9, the calibration curve (1) and the calibration curve (2) used in the first embodiment of the present invention are also shown.

As shown in FIG. 9, a relatively high concentration range of the calibration curve (α) simulates the calibration curve (1) in which the prozone-like phenomenon is absent, whereas a relatively low concentration range of the calibration curve (α) simulates the calibration curve (2) which provides high repeatability. Therefore, the use of the calibration curve (α) provides the same advantage as those obtained by the first embodiment of the present invention. Further, the detection of the prozone-like phenomenon or the process step for selecting a calibration curve is not required.

The foregoing description of the embodiments is given with respect to an example of concentration computation based on optical responses. However, depending on the kind of the reaction system, the present invention is also applicable to concentration computation based on electrical responses obtained when a voltage is applied to the reaction system or a current is caused to flow through the reaction system, a frequency change in accordance with the progress of the reaction, a thermal response when light or vibration is applied to the reaction system, for example.

In the first and the second embodiment, the case in which the prozone-like phenomenon occurs is exemplarily described. However, the present invention is also applicable to the case in which the resolving power is reduced in a high concentration range. Specifically, in the concentration measurement performed by using a reaction system whose absorbance asymptotically approaches a constant value in a high concentration range, the present invention enables proper concentration measurement for the high concentration range.

The invention claimed is:

1. A concentration measuring method comprising: selecting a calibration curve optimum for computing concentration of a measurement target substance from a plurality of calibration curves based on an output from a reaction system containing the target substance and a reactant capable of reacting with the target substance; and computing the concentration of the target substance based on the optimum calibration curve and the output;
   wherein each of the calibration curves is prepared based on a plurality of outputs generated upon lapse of a same reaction time from a plurality of standard reaction systems each containing a standard reagent of a known different concentration and the reactant;
   wherein the plurality of calibration curves differ from each other in reaction time based on which the calibration curves are prepared;
   wherein the plurality of calibration curves include a first calibration curve to be selected when the concentration of the target substance is predicted to be higher than a predetermined concentration threshold, and a second calibration curve to be selected when the concentration of the target substance is predicted to be lower than the concentration threshold;
   wherein the first calibration curve is prepared based on an output measured in an initial stage of the reaction between a standard substance of a known concentration and the reactant; and
   wherein the second calibration curve is prepared based on an output measured after the output as the base for the preparation of the first calibration curve is measured.

2. The concentration measuring method according to claim 1, further comprising the steps of: computing a second concentration by using the second calibration curve, comparing the second concentration with a first concentration computed by using the first calibration curve when the second concentration is predicted to be higher than the concentration threshold, and adopting a higher one of the first and second concentrations as a conclusive computation value.

3. The concentration measuring method according to claim 1, further comprising the steps of: computing a second concentration by using the second calibration curve for determining whether or not the second concentration reflects the concentration of the target substance when the second concentration is predicted to be lower than the concentration threshold;
   adopting the second concentration as a conclusive computation value when the second concentration reflects the concentration of the target substance; and
   computing a first concentration by using the first calibration curve for adopting the first concentration as a conclusive computation value when the second concentration does not reflect the concentration of the target substance.

4. The concentration measuring method according to claim 1, further comprising the steps of: computing a first concentration by using the first calibration curve for adopting the first concentration as a conclusive computation value when the first concentration is predicted to be higher than the concentration threshold; and
   computing a second concentration by using the second calibration curve for adopting the second concentration as a conclusive computation value when the first concentration is predicted to be lower than the concentration threshold.

5. The concentration measuring method according to claim 1, wherein whether the concentration of the target substance is higher or lower than the concentration threshold is predicted based on whether or not the output is higher than a predetermined output threshold.

6. The concentration measuring method according to claim 1, wherein the concentration threshold is set to lie in a concentration range in which the second calibration curve has high linearity.

7. The concentration measuring method according to claim 1, wherein the concentration threshold is set to a concentration corresponding to an intersection of the first calibration curve and the second calibration curve.

8. The concentration measuring method according to claim 1, wherein the output is an optical response obtained when the reaction system is irradiated with light.

9. A concentration measuring method for computing concentration of a measurement target substance based on an output from a reaction system containing the target substance and a reactant capable of reacting with the target substance, and a specific calibration curve showing a relationship between the concentration of the target substance and the output;
   wherein the specific calibration curve is prepared as a composite of a first calibration curve and a second calibration curve, the first calibration curve being prepared based on an output measured in an initial stage of the reaction between a standard substance of a known concentration and the reactant, the second calibration curve being prepared based on an output measured after the output as the base for the preparation of the first calibration curve is measured; and
   wherein the specific calibration curve comprises a higher concentration portion for a concentration range higher than an intersection concentration which corresponds to an intersection of the first calibration curve and the second calibration curve, and a lower concentration portion for a concentration range lower than the intersection concentration, the higher concentration portion comprising a portion of the second calibration curve for a concentration range higher than the intersection concentration, the lower concentration portion comprising a portion of the first calibration curve for a concentration range lower than the intersection concentration.

10. The concentration measuring method according to claim 9, wherein the output is an optical response obtained when the reaction system is irradiated with light.

11. A concentration measuring method comprising: selecting a calibration curve optimum for computing concentration of a measurement target substance from a plurality of calibration curves based on an output from a reaction system containing the target substance and a reactant capable of reacting with the target substance; and computing the concentration of the target substance based on the optimum calibration curve and the output;

wherein each of the calibration curves is prepared based on a plurality of outputs generated upon lapse of a same reaction time from a plurality of standard reaction systems each containing a standard reagent of a known different concentration and the reactant;

wherein the plurality of calibration curves differ from each other in reaction time based on which the calibration curves are prepared;

wherein the plurality of calibration curves are prepared by measuring, at a plurality of measurement time points, outputs from the plurality of standard reaction systems each containing a standard reagent of a known different concentration and the reactant, each of the calibration curves corresponding to a respective one of the measurement points; and wherein the selection of the optimum calibration curve is performed based on an output measured in a time period in which the reaction between the target substance and the reactant is in an initial stage.

* * * * *